United States Patent [19]
Sylvester et al.

[11] 4,112,775
[45] Sep. 12, 1978

[54] FILLET WELD INSPECTION SYSTEM

[75] Inventors: Bruce J. Sylvester, Duxbury; Roger P. Sylvester, Kingston, both of Mass.

[73] Assignee: J. G. Sylvester Associates, Inc., Rockland, Mass.

[21] Appl. No.: 792,063

[22] Filed: Apr. 28, 1977

[51] Int. Cl.² ............................................. G01N 29/04
[52] U.S. Cl. ........................................ 73/627; 73/644
[58] Field of Search ......................... 73/67.7, 627, 644

[56] References Cited

U.S. PATENT DOCUMENTS 2,799,157   7/1957   Pohlman ................................ 73/67.7

FOREIGN PATENT DOCUMENTS 716,687   10/1954   United Kingdom ..................... 73/67.7

OTHER PUBLICATIONS

Krautkramer et al., pp. 500–504 of Textbook-Werkstoffprufung mit Ultraschall-Pub. 1975, Springer-Verlag.

Primary Examiner—Richard C. Queisser
Assistant Examiner—John P. Beauchamp
Attorney, Agent, or Firm—David G. Conlin

[57] ABSTRACT

A device for underwater detection of flaws in welds, especially lap welds as distinguished from butt welds wherein a filleted weld is made, said device embodying ultrasonic transducers arranged to emit and receive a sonic beam at angles such as to pass through the weld at an angle corresponding substantially to the inclination of the weld and to be adjustable for welds of different inclination and for beam travel through different configurations of weldments.

9 Claims, 6 Drawing Figures

FILLET WELD INSPECTION SYSTEM

BACKGROUND OF THE INVENTION

In underwater repair operations, fillet welds are used extensively due to the relative ease of installing of a fillet weld as opposed to installing a butt weld. A butt weld takes more skill on the part of the welder and is more susceptible to defects due to the varying influences encountered in the underwater environment. For example, if a crack is found in an underwater structure such as the hull of a ship, it is generally preferred to weld a "doubler" or additional plate over the cracked area using a fillet weld than it is to cut out the hull plate around the defective area and install a sound piece of plate in its place. Although the butt weld will give a smoother contour to the hull, the ship must be dry-docked during the operation or else a watertight habitat must be built around the defective area. Moreover, the defective material that is cut out must be discarded without damaging the habitat and a new piece of plate must be cut to size to exactly fit the hole where the damaged plate was removed and the diver must have access into and out of the habitat without disturbing the watertight environment. The new plate must be carefully held in alignment during the initial stages of welding and the welder has to weld into an "open groove" with poor edge preparation and no backing. Any water, oil, grease or other bilge on the interior of the ship must be drained and cleaned to bare the metal in the welding area.

In constrast, a double plate type of repair may be performed in the wet, that is, underwater, with minimum cleaning and edge preparation, is uncomplicated and requires only minor skill on the part of the welder. Thus, fillet welding doubler plates is eminently more practical in terms of expense, time and quality of the end result and so is used in almost all repair operations performed underwater.

Devices for ultrasonic inspection have been used extensively on land and, to some extent, underwater in determining the quality of butt welds; however, ultrasonic inspection of "fillet" or "lap" welds has not been effectively developed. The reason for this is the inherent geometry of the lap joint which does not lend itself to the current methods of straight beam or shear wave inspection, and fillet welds generally are used on less critical joints where inspection has not been required. Recently, however, because of more stringent quality control of repair operations, the need for a device for providing for better inspection of fillet welds has risen, since that used for butt welds is not suitable. It is the purpose of this invention to provide inspection means designed particularly to enable accurate determination of the conditions of fillet welds, including such defects as lack of penetration, lack of fusion, slag inclusions, porosity, cracks, intergranular cracking of the weld and base metal, corrosion, stress corrosion cracks, inclusions and other defects.

SUMMARY OF THE INVENTION

The device as herein illustrated is for detecting flaws in a fillet weld joining two parts in overlapping relation and comprises a first transducer, a support for supporting said first transducer at one side of the parts at an angle such that the beam emitted therefrom travels from the one side to the other of the overlapping parts and is reflected by the part at the other side back to the support at the one side, and at a point therealong spaced from the first transducer such that during the course of its travel, the beam pass through the weld along a path substantially parallel to the inclined surface of the weld and means mounting a second transducer on the support at said point at an angle to receive said reflected beam. A carriage block is mounted on the support for movement relative to one end of the support, and means are provided for fixing the carriage block in a predetermined adjusted position. The support and carriage block contain longitudinally aligned openings from top to bottom in which the transducers are adjustably fixed at converging angles, e.g., of approximately 18 degrees from the vertical when the inspection is done using water as the couplant.

The invention will now be described in greater detail with reference to the accompanying drawings, wherein:

FIG. 1 diagrammatically illustrates the device for detecting imperfections in a lap or filleted joint;

FIG. 2 is a perspective of the device;

FIG. 3 is an elevation of a cathode ray screen wherein the peak at the left-hand side represents the sound at the entry point and the peak at the right-hand side the sound received and wherein the distance between peaks represents the total distance of the sound path through the media and the height of the right-hand peak represents the amount or quality of the sound received by the receiving transducer;

Figure 1:
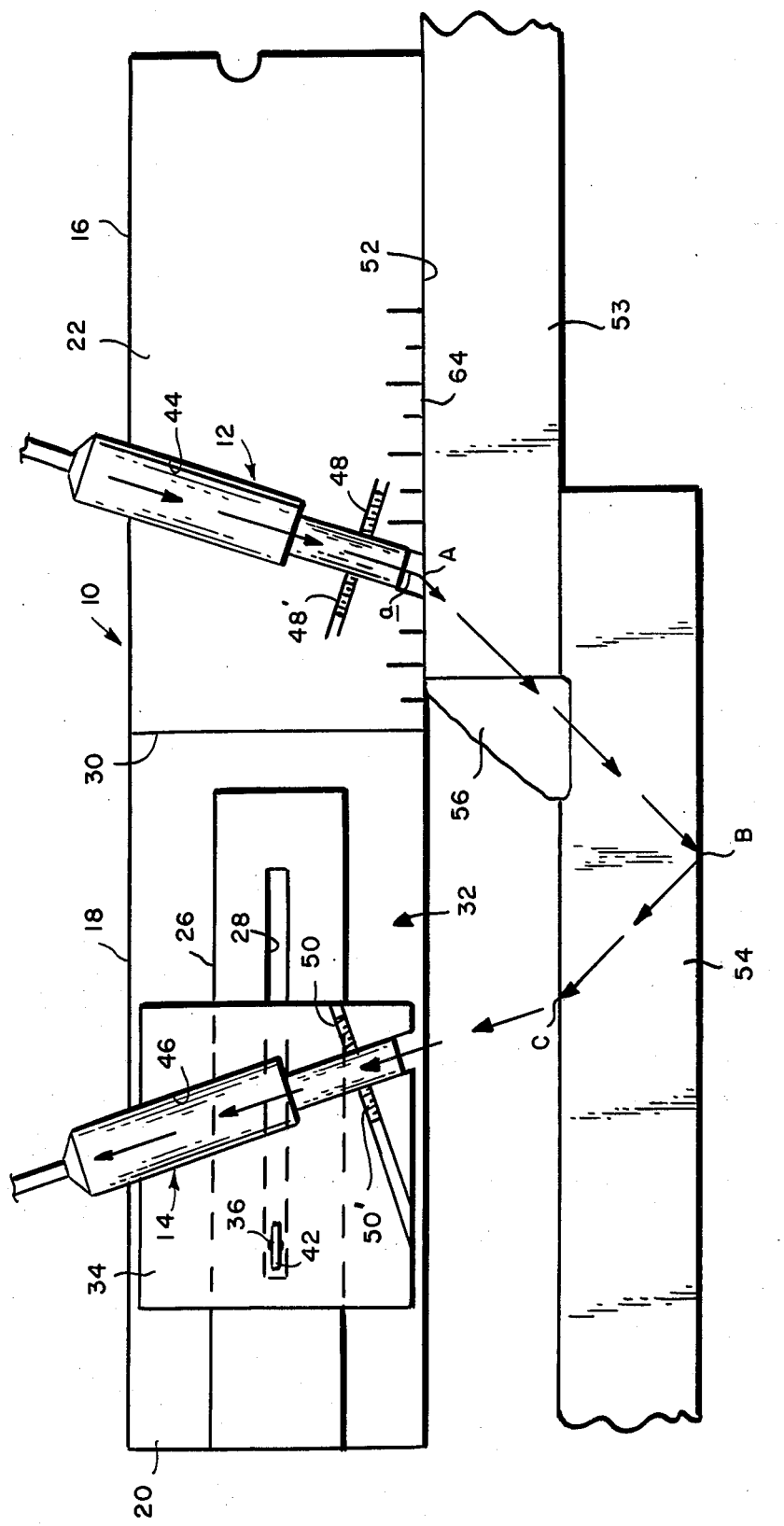
Figure 2:
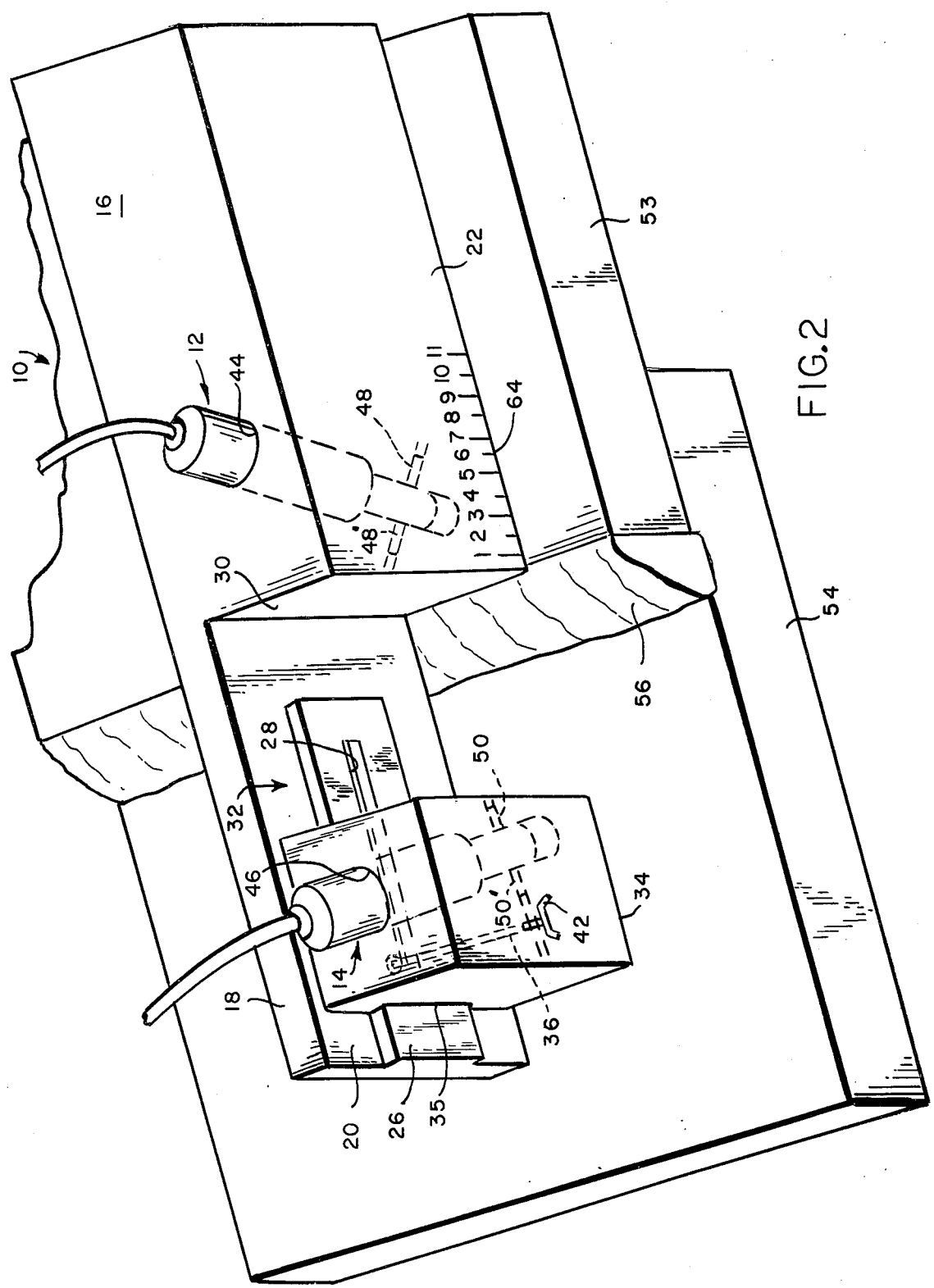

Referring now to the drawings, FIGS. 1 and 2, one embodiment of the invention is disclosed, wherein the device comprises a support 10 mounting two transducers 12 and 14 in longitudinally spaced relation at converging angles such that, in use, when the device is moved across and along the fillet at one side, the beam emitted from one transducer will enter the part at the one side, pass through the fillet along a path substantially parallel to the inclined surface thereof and through the other part at the other side, be reflected in said part at the other side and transmitted therethrough at an angle to be received by the other transducer.

The support 10 as illustrated herein comprises an elongate, rigid block 16 of rectangular cross section at one end of which there is an extension 18 of a narrower front-to-back width, the rear side of which is a continuation of the rear side of the block 16 and the front side 20 of which is situated rearwardly of the front side 22 of the block 20 and parallel thereto. The front side 20 of the extension has a forwardly-projecting, longitudinally-extending tongue 26 parallel to the upper and lower sides of the block and its extension and longitudinally of the tongue, there is an elongate slot 28 which extends through the extension from the front side of the tongue to the back side of the extension. The front side 20 of the extension and the end 30 of the block from which it extends define a recess 32 and a carriage block 34 is mounted in the recess on the tongue for sliding movement along the extension relative to the end 30 of the block. The carriage block 34 corresponds substantially in front-to-back width to the depth of the recess 32 and is provided at its rear side with a groove 35 for slidably engaging the tongue so that it is guided rectilinearly in its movement relative to the block 16. The carriage block is adjustably secured to the extension by a bolt 36 provided with a head 38 at one end which is mounted in the slot 28 with its shank extending forwardly through a hole 40 in the block and has on its forwardly-projecting end a nut 42.

The supporting block 16 and carriage block 34 contain longitudinally aligned openings 44 and 46 which extend from the top to the bottom for receiving the transducers 12 and 14. Set screws 48 – 48' and 50 – 50' provide for fixing the transducers 12 and 14 in the openings and for adjusting them therein to provide the proper inclination of the transducers relative to each other. The openings 44 and 46 are inclined at corresponding angles of approximately 18 degrees to the vertical when the coupling medium which is used to transmit the sound between the transducer and the article to be inspected is water, the article to be inspected is steel, and the desired angle of transmission of the sound through the article to be inspected is 45 degrees. This angle may be adjusted for other conditions in accordance with the indices of refraction of the coupling medium and the material to be inspected, as will be apparent to those skilled in the art.

Figure 6:
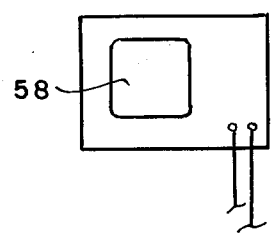
FIG. 6 is an ultrasonic generator provided with a cathode ray screen on which the signals are depicted.

The transducer 12 emits an ultrasonic beam and, as disclosed in FIG. 1, is arranged so that when the device is placed in parallel relation to the lap joint to be tested with its bottom planar surface 52 resting on a plate 53, for example, which has been lap-welded to a plate 54 by means of a fillet weld 56, a beam $a$ emitted from the transducer 12 will enter the plate 53 at the point A, pass through the weld 56 at approximately 45°, and from thence through the plate 54 to the point B, whereupon it will be reflected through an angle of approximately 90° so as to recross the plate 54, leave the plate 54 at the point C and enter the transducer 14. If the weld is sound, the beam $a$ transmitted through it will be substantially unimpeded so that a strong signal substantially as strong as that emitted from the transducer 12 will be received by the transducer 14, indicating the absence of defects. Such a signal is represented by the peak marked II in FIG. 3 of the drawings which is nearly as high as the peak marked I which represents the strength of the signal emitted from the transducer 12. The presence of a defect, of course, will result in dispersion of the beam to a certain extent and, depending upon the attenuating qualities of the defect, will result in a diminution of the signal as represented, for example, in FIG. 4. A serious defect will normally result in complete dispersion of the signal as represented in FIG. 6 or will indicate that the device has been moved beyond the area of the weld.

Figure 3:
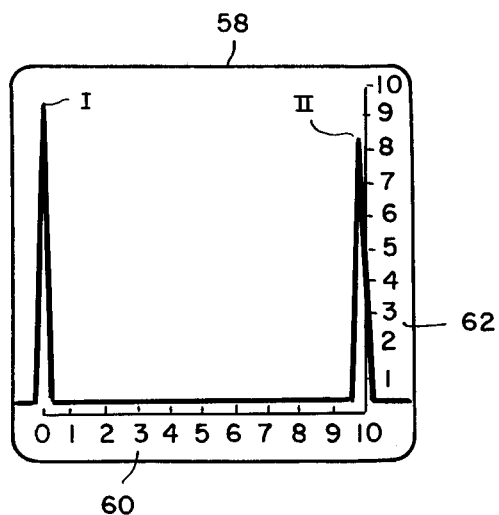
Figure 4:
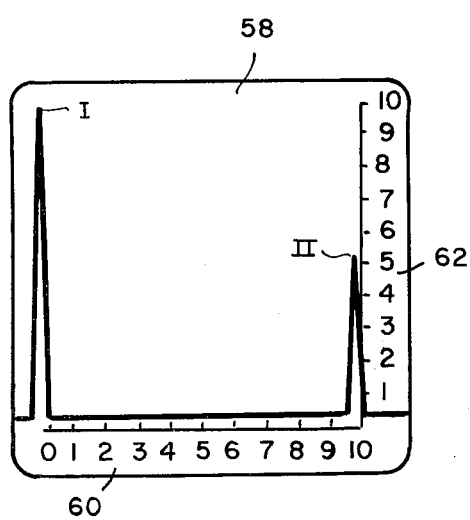
FIG. 4 is similar to FIG. 3 showing the peak at the right-hand side of the screen much lower than the peak at the left-hand side, thus indicating poor sound reception and thus the presence of a defect.
Figure 5:
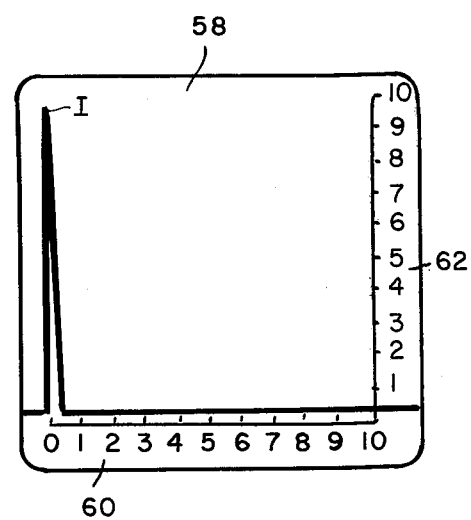
FIG. 5 shows the peak at the left-hand side with no peak at the right-hand side, indicating a major defect which has dissipated the beam entirely or that the device has been moved beyond the area of the weld.

The signals transmitted and received by the transducers are graphically displayed e.g., on a cathode ray screen 58 such as is shown in FIGS. 3, 4 and 5 which has along the vertical edge a scale 62 representing the strength of the signal. The distance between the peaks I and II represents the total distance of the sound travel through the media. The height of the first peak I is a constant in that it simply indicates the strength of the signal produced by the first transducer. The height of the second peak II is directly proportional to the amount of the signal received by the second transducer.

The adjustment of the carriage block 34 along the extension and, hence, of the transducers relative to each other provide for use of the device with lap welds and base materials of different thickness. For a particular article to be inspected, having known thickness and composition, the inspecting device can conveniently be placed on the article, or on a calibration block machined to duplicate the ideal properties thereof, and the distance between the transducers varied to achieve maximum signal reception.

As previously indicated, the angle at which the transducers are set is chosen to correspond to the angle of refraction and angle of incidence of the media in which the device is to be used, which for water and steel is approximately 18° to achieve a 45° angle transmission through the steel. The set screws 48–48' and 50-50' enable changing the angle of the transducers to adjust the angles of refraction and incidence for varying media conditions and test requirements, and openings 44 and 45 are sufficiently large to permit such angular adjustment (not shown) of the transducers 12 and 14.

Since water is an excellent transmitter of sound, there is no need for the use of a separate coupling medium between the transducers and the plates which are to be inspected, when the inspection is performed underwater. If, however, the device is to be used on dry land, coupling means would have to be employed to conduct the beams from the transducers to the parts to be inspected. One means of providing the necessary coupling would be to supply water to the lower part of openings 44 and 46, to maintain a continuous water phase or flush between the face of the transducers and the article to be inspected, thus providing an uninterrupted sound path between the transducers and article's surface. In this regard, for use in dry environment application, the carriage block 34 may conveniently be made adjustable vertically, in addition to the horizontal adjustability provided by slot 22 as shown so as to permit the transducer 14 to be moved closer to the article's surface. Other suitable coupling means for use in a dry or land based inspection environment will be apparent to those skilled in the art.

The support 10 may be made of any suitable material, preferably one which is not corroded in the environment of use, and most preferably, one which is transparent, to permit observation of the device in operation. Suitable materials include transparent plastics such as Plexiglas or Lucite.

The transducers are selected for sensitivity penetration qualities and resolution and those illustrated herein are, for example, 5MHZ ½ inch diameter transducers. A wide variety of types of transducers are commercially available. Ultrasonic devices to which the transducers are connected by coaxial conductors are also readily available commercially, a suitable device being a Krautkramer Model 303B, manufactured by Krautkramer-Branson Company of Bridgeport, Conn.. One such device is shown diagrammatically in FIG. 6 equipped with a cathode ray screen 58 such as shown in FIGS. 2, 3 and 4.

While the particular embodiment has been described using transducer 12 as the ultrasonic beam transmitter and transducer 14 as the receiver, they could also be used in reverse roles. In some circumstances, it may be advantageous to have the two transducers switch roles intermittently, thus having the sound pass through the article first one way and then the other.

The technique in using the device is to push it back and forth across and along the weld, observing the heights of the peak No. II as the weld is traversed. A scale 64 may be provided on the front side 22 of the supporting block 10 which is calibrated prior to the inspection and indicates for any given configuration of material the position of the sound travel through the weld relative to the interface of the edge of the weld and the plate. If, within this range, a loss in the height of the second peak is observed, it indicates an unsatisfactory condition such as lack of fusion or weld penetration.

It should be understood that the present disclosure is for the purpose of illustration only and includes all modifications or improvements which fall within the scope of the appended claims.

I claim:

1. An instrument for detecting defects in lap welds comprising a rigid, elongate block having a bottom planar surface and containing a recess in its front side which extends from one end to substantially the midlength of the block, said unrecessed portion of the block containing an opening from the top to the bottom, a first transducer mounted in said opening, a carriage block slidably mounted to the block in the unrecess for linear movement relative to the unrecessed portion, said carriage block containing an opening from top to bottom, a second transducer mounted in the opening in the carriage block in alignment with the first transducer, said first and second transducers being capable of generating and detecting ultrasonic beams, and means for adjusting the distance between the transducers by movement of the carriage block in the recess relative to the unrecessed portion of the block, said openings being inclined to the bottom planar surface at converging angles corresponding to the angles of incidence and refraction of the ultrasonic beams transmitted through the couplant medium with which the instrument is to be used.

2. A device according to claim 1 wherein the transducers are mounted at angles such that the beam travels through the weld at approximately 45° to the side surfaces thereof.

3. A device according to claim 1 wherein the couplant medium is water.

4. A device according to claim 1 wherein the transducers are mounted at converging angles of approximately 18° from the vertical.

5. A device according to claim 1 wherein the block has along the unrecessed portion a scale representing the position of the sound travel through the work through which the beam is to be transmitted.

6. A device according to claim 1 wherein the recess has a tongue projecting from its face and the carriage block a groove slidingly engaged with the tongue and where there is a locking element for locking the carriage block at a predetermined select position on the block.

7. An instrument for detecting defects in the lap welds comprising a rigid, elongate supporting block, an extension at one end of said block of lesser front-to-back thickness, the front face of the extension in conjunction with the end of the block from which the extension extends defining a recess at the front side of the block, a carriage block mounted in the recess for movement linearly relative to the end of the block from which the extension extends, said supporting block and said carriage block containing longitudinally aligned openings, inclined in converging relation to the bottom planar surface of the supporting block at angles corresponding to the angles of refraction and incidence of the medium within which the device is to be used, transducers mounted in the openings, and means for adjusting the carriage block in the recess to vary the spacing of the transducers and to fix them at a predetermined spacing.

8. A device according to claim 7 comprising a cathode ray screen and means for displaying signals emitted and received by the transducers on the screen for comparison.

9. An instrument according to claim 7 wherein said cathode ray screen is provided along one edge with a scale indicating the distance the signal travels and along another edge with a scale indicating the relative magnitude of the signals.

* * * * *